(12) United States Patent
Yi

(10) Patent No.: US 7,270,982 B2
(45) Date of Patent: Sep. 18, 2007

(54) HELICOBACTER PYLORI ANTIGENS IN BLOOD

(75) Inventor: Ching Sui A. Yi, Taoyuan (TW)

(73) Assignee: Joy Biomedical Corporation, Taoyuan (TW)

( * ) Notice: Subject to any disclaimer, the term of this patent is extended or adjusted under 35 U.S.C. 154(b) by 36 days.

(21) Appl. No.: 10/922,263

(22) Filed: Aug. 20, 2004

(65) Prior Publication Data

US 2005/0009108 A1 Jan. 13, 2005

Related U.S. Application Data

(63) Continuation-in-part of application No. 10/041,510, filed on Jan. 10, 2002, now Pat. No. 6,794,153, which is a continuation-in-part of application No. 09/572,598, filed on May 17, 2000, now abandoned.

(60) Provisional application No. 60/170,537, filed on Dec. 14, 1999.

(51) Int. Cl.
    C12P 19/34 (2006.01)
(52) U.S. Cl. .............. 435/91.2; 435/6; 435/91.1; 435/91.21; 536/23.7; 536/24.3; 536/24.32; 536/24.33; 204/182.1
(58) Field of Classification Search .......... 435/6, 435/91.2, 91.1, 91.21; 536/23.7, 24.3, 24.32; 536/24.33; 204/182.8
    See application file for complete search history.

(56) References Cited

U.S. PATENT DOCUMENTS

| 5,527,678 | A | * | 6/1996 | Blaser et al. .............. 435/6 |
| 5,716,791 | A | | 2/1998 | Larka et al. |
| 5,871,942 | A | | 2/1999 | Larka et al. |
| 5,932,430 | A | | 8/1999 | Larka et al. |
| 6,153,390 | A | | 11/2000 | Cover et al. |
| 6,245,516 | B1 | * | 6/2001 | Al Rashid et al. .............. 435/6 |

FOREIGN PATENT DOCUMENTS

| EP | 0 329 570 | 8/1989 |
| EP | 0 806 667 | 11/1997 |
| WO | WO99/41611 | 8/1999 |
| WO | WO 00/29432 | 5/2000 |

OTHER PUBLICATIONS

Lu et al (J.Clin.Microbiol., Mar. 199. 37(3): 772-774).*
Blasi et al (JID. Dec. 1, 1999. 180: 2074-2076).*
Marshall, Barry; *Helicobacter pylori*—The Etiologic Agent for Peptic Ulcer; JAMA, Oct. 4, 1995, vol. 274, No. 13, p. 1064-1066.
Howden, Colin; Testing for *H. pylori* in the Post-treatment Period; The American Journal of Medicine, May 20, 1996, vol. 100 (suppl 5A), p. 5A-39S-5A-41S.
Cutler, Alan; Testing for *Helicobacter pylori* in Clinical Practice; The American Journal of Medicine, May 20, 1996, vol. 100 (suppl 5A), p. 5A-35-5A-38S).

Jang-Jih Lu et al.; Comparison of five PCR method for detection of *Helicobacter pylori* DNA In gastric tissues; Journal of Clinical Microbiology, vol. 37, No. 3, Mar. 1999, pp. 772-774.
Genta, Robert; Simultaneous Visualization of *Helicobacter pylori* Gastric Morphology: a New Stain; Human Pathology, Mar. 1994, vol. 25, No. 3, p. 221-226.
Han. S.W.: Transport and Storage of *Helicobacter pylori* from Gastric Mucosal Biopsies and Clinical Isolates; Eur. J. Clin. Microbiol. Infect. Dis., vol. 14, 1995, p. 349-352.
Tomb, J.F. et al., Nature, vol. 388, pp. 539-547.
Danesh, J., et al., The Lancet, vol. 350 (9075), pp. 430-436 (abstract).
Hsueh, P.R., et al., Journal of Clinical Microbiology, vol. 37(6), pp. 2084-2086 (abstract).
Hung, C.C., et al., Journal of Formosan Medical Association, vol. 96(7), pp. 558-560, (abstract).
Husmann, M., et al., Journal of Clinical Microbiology, vol. 32(12), pp. 3037-3039.
Kemper, C.A., et al., Journal of Infection, vol. 26(1), pp. 97-101.
Lastovica, A.J., et al., Abstracts of the General Meetingof the American Society of Microbiology, vol. 97(0), pp. 168, May 4-8 (abstract).
Ndawula, E.M., et al., European Journal of Clinical Microbiology and Infectious Diseases, vol. 13(7), p. 621, July (abstract).
Negrini, R., et al., Gastroenterology, Sep. 1996, vol. 111(3), pp. 655-665, (abstract).
Kiehlbauch, J.A., et al., Annals of Internal Medicine, vol. 121(2) pp. 90-93, Jul. 15, (abstract).
Orticek, S.L., et al., Journal of Clinical Microbiology, vol. 31(3), pp. 569-571, Mar. 1993 (abstract).
Tee, W., et al., Scandinavian Journal of Infectious Diseases, vol. 28(2), pp. 199-203, (abstract).
Trivett-Moore, N.L., et al., Journal of Clinical Microbiology, vol. 35(5), pp. 1144-1150, May 1997 (abstract).
O'Toole, P.W., Isolation and Biochemical and Molecular Analysis of a Species-Specific Protein Antigen from the Gastric Pathogen *Helicobacter pylori*, vol. 173, No. 2, pp. 505-513, Jan. 1991.

* cited by examiner

Primary Examiner—Jennifer E. Graser
(74) Attorney, Agent, or Firm—Fei-Fei Chao; Andrews Kruth, LLP

(57) ABSTRACT

The present invention provides methods for detecting *Helicobacter pylori* (*H. pylori*) DNA and/or fragments thereof in blood. The first method involves extracting DNA from a blood sample, preferably plasma, by amplifying the DNA using a polymerase chain reaction (PCR) or a ligase chain reaction (LCR) method, and detecting a target DNA sequence in the amplified DNA. The preferred target DNA sequence comprises a Mr26 or a 16S rRNA gene or fragments thereof specific to *H. pylori*. The second method involves extracting DNA from a blood sample, preferably serum, by hybridizing the extracted DNA with a radioisotope or fluorescence labeled *H. pylori* DNA probe.

4 Claims, 2 Drawing Sheets

HELICOBACTER PYLORI ANTIGENS IN BLOOD

RELATED APPLICATION

The present application is a continuation-in-part (CIP) application which claims the priority of U.S. patent application Ser. No. 10/041,510, now U.S. Pat. No. 6,794,153, filed on Jan. 10, 2002, which is a CIP of U.S. patent application Ser. No. 09/572,598, filed on May 17, 2000, now abandoned, which in turn claims the priority of U.S. Provisional Patent Application Ser. No. 60/170,537, filed on Dec. 14, 1999. The contents of the parent applications are herein incorporated by reference.

FIELD OF THE INVENTION

The present invention relates to methods for detecting Helicobacter pylori (H. pylori) DNA in blood. The first method requires extracting DNA from a blood sample, preferably plasma, in humans, by amplifying the DNA using a polymerase chain reaction (PCR) or a ligase chain reaction (LCR) method, and detecting a target DNA sequence in the amplified DNA. The preferred target DNA sequence comprises a Mr26 or a 16S rRNA gene or fragments thereof specific to H. pylori. The second method involves extracting DNA from a blood sample, preferably serum, in humans, by hybridizing the extracted DNA with a radioisotope or fluorescence labeled H. pylori DNA probe.

BACKGROUND OF THE INVENTION

Helicobacter pylori (H. pylori) is a curved or spiral gram-negative bacterium which infects the gastric mucosal and is responsible for most peptic ulcer disease (PUD). Since this first isolation, Until recently, ulcers and other forms of dyspepsia were thought to be related to stress levels or eating habits. Recently, the medical community has confirmed that H. pylori is the causative agent for certain forms of gastric distress, including ulcers and gastric cancer. Eradication of H. pylori promotes healing of ulcer and greatly reduces the incidences of cancer and PUD.

H. pylori causes most gastric and duodenal ulcers, as well as peptic ulcer disease (PUD). The linkage of H. pylori and PUD was first discovered and published by Australian physicians Warren and Marshall in 1984 (Lancet I: 1311-1344). The H. pylori infection is now accepted as the most common cause of gastritis, and is etiologically involved in gastric ulcer, duodenal ulcer, gastric adenocarcinoma and primary B-cell lymphoma.

It has been proven that PUD is curable and rather easily. The cause of most PUD is infection with H. pylori. However, H. pylori infection is not routinely diagnosed, possibly because methods of testing for H. pylori infection are not satisfactory to physicians, especially the primary care physicians (i.e. invasive biopsy test). Therefore, primary physicians have tended to treat symptomatic patients with antisecretory agents.

Physicians need a simple, accurate and inexpensive diagnostic test for H. pylori infection so that they know when to treat patients and when to refer the patients to a gastroenterologist. However, the currently available H. pylori tests, which can be categorized as invasive tests and noninvasive tests, are not completely satisfactory.

The invasive tests require the use of endoscope followed by biopsy procedure. The tissue samples taken by the biopsy procedure can then be analyzed by culture, histology, or rapid urease testing.

Although culturing of the biopsy specimens provides the most reliable results for H pylori testing, the reports of successful rates in a good laboratory are only between 70% and 80% (Han, S. W., et al., Eur. J. Clin. Microbiol. Infect. Dis. (1995), 14:349-352). Histological examination of special stained biopsy specimens can provide the direct evidence of acute or chronic inflammatory mucosal cells and lesions. However, it requires the collaborations of both an endoscopist and a pathologist (Genta, R. M., et al., Hum. Pathol. (1994), 25:221-226). Rapid urease tests detect the rise in pH from ammonia produced by H. pylori urease, which splits urea into ammonia and carbon dioxide. However, it requires a high density of bacteria and anything that reduces the bacterial load may produce a false-negative (Cutler, A. F., Am. J. Med. (1996), 100:35S-39S).

A number of noninvasive tests have been developed to detect the presence of H. pylori infection since 1990. For example, the Urea Breath Testing is based on the urease activity of the organism, which splits urea labeled with $^{13}C$ or $^{14}C$ into nonradioactive $^{13}CO_2$ or radioactive $^{14}CO_2$. The urea breath test is widely recommended for confirming eradication of H. pylori 4 weeks after therapy.

U.S. Pat. Nos. 5,716,791, 5,871,942, and 5,932,430 disclose immunoassays for detecting H. pylori antigens in stool specimens using a polyclonal antibody which is obtained from sensitizing animal with H. pylori cells (i.e., ATCC strain 43504). The antibody is purified by DEAE (diethylaminoethyl cellulose) column. Although the stool antigen test is reported to be satisfactory, the collection and process of the stool specimens are found to be difficult and unpleasant. Many patients are unwilling to provide stool samples to physician due to offensive odor and lack convenient collection device.

Serologic testing of serum H. pylori antibodies using ELISA is another widely used test. Examples of the latter techniques can be found in a U.S. Pat. No. 5,262,156 and EP Pat. No. 0 329 570. There have been several major antigens identified and used in immunoassays in the detection of H. pylori antibodies. However, these assays have not exhibited the specificity and sensitivity that are desired in serodiagnosis. (Newell, D. G., et al., Serodian. Immunother. Infec. Dis., (1989), 3:1-6). One of the problems derives from cross-reactivity. That is because the dominant antigens in H. pylori (e.g., the putative flagellar protein which has a molecular weight of 60 Da) are not specific to H. pylori. Some of these antigens can be found in other bacteria such as C. jejuni and C. coli. A second problem that has been encountered in designing immunoassays for H. pylori is strain variation. Substantial differences in the antigens have been observed in different strains of H. pylori. These problems preclude designing an assay around the use of a single antigen. One approach that has been taken to improving the specificity and selectivity of antibody immunoassays for H. pylori has been to use a mixture of antigens from different H. pylori strains which mixture is enriched with certain antigen fragments. One ELISA which detects H. pylori antibodies in blood sera is commercially available. This assay uses a bacterial whole cell lysate as the antigen.

There are other disadvantages of using an ELISA which employs antigens to detect the presence of H. pylori antibodies in serum. In particular, the antibody titer in human sera remains high for a prolonged time (in some cases as much as twelve months) after the infection has been treated. Consequently, a positive test using this ELISA does not necessarily mean that the patient is currently infected and requires treatment for H. pylori infection. When confronted with a positive ELISA, treating physicians often order a gastric biopsy to confirm the presence of the bacteria before initiating antibiotic therapy. Therefore, the antigen-based ELISA does not eliminate the need for the invasive procedure.

It is therefore the object of the present invention to design a noninvasive and highly accurate diagnostic test for *H. pylori* infection. During the course of the investigation, *H. pylori* antigens in blood are discovered, which are in the forms of DNA or fragments thereof, or proteins/peptides or other antigenic components thereof, exist in blood, including whole blood, plasma and serum. Special methods for detecting these *H. pylori* antigens are thus designed to provide evidence that antigenic fragments of *H. pylori* are existed in blood. These methods include, but not limited to, polymerase chain reaction (PCR), ligase chain reaction (LCR) and DNA hybridization for detecting nucleic acid fragments of *H. pylori*, using primers or oligonucleotides specific for *H. pylori* and/or DNA probes derived from *H. pylori* strains. Additionally, immunoassays and immunoblotting are also developed for detecting protein/peptide or any antigenic components of *H. pylori*, using an affinity purified antibody against *H. pylori*.

There has been no report with regard to the existence of *H. pylori* antigens in blood. The present invention is the first to prove that *H. pylori* antigens not only exist in blood, but can be detected by the methods presented in the following sections

SUMMARY OF THE INVENTION

The present invention provides methods for detecting *Helicobacter pylori*—(*H. pylori*) specific DNA or fragments thereof in a blood sample of a human.

In one embodiment, the detection method comprises the steps of: (a) obtaining a blood sample from a human; (b) extracting DNA from the blood sample; (c) amplifying the DNA to produce an amplified DNA; and (d) detecting the presence of a target DNA sequence, which is specific to *H. pylori*, in the amplified DNA. The blood sample for this method is preferably plasma. The DNA can be extracted by any conventional methods, including, but not limited to, phenol-chloroform extraction, or methods employing proteolytic digestion, such as using proteinase K in commercial kit (QIAamp blood Mini Kit, manufactured and sold by QIAGEN).

The extracted DNA is amplified DNA by a polymerase chain reaction (PCR) using a pair of primers specific to *H. pylori*; or by a ligase chain reaction (LCR) using a first set of two adjacent oligonucleotide probes and a second set of complementary oligonucleotide probes specific to *H. pylori*.

The preferred target DNA sequence comprises a Mr26 gene (Gene Bank accession number: M55507) or fragments thereof specific to *H. pylori*. The Mr26 gene encodes a protein which is about 26 KDa with about 232 residues and about 696 base pairs To detect the presence of the Mr26 gene in a human blood sample, the extracted DNA is amplified with a polymerase chain reaction (PCR) using a pair of primers specific to the Mr26 gene, which includes, but is not limited to, HPMr3 having the DNA sequence of SEQ ID NO:1 and HPMr4 having the DNA sequence of SEQ ID NO:2. The PCR is further run by a second pair of primers, which includes, but is not limited to, HPMr1 having the DNA sequence of SEQ ID NO:3 and HPMr2 having the DNA sequence of SEQ ID NO:4. The PCR product of the Mr26 gene that has been detected in the patient's blood sample is about 190 base pairs in length.

Another preferred target DNA sequence comprises a 16S rRNA gene or fragments thereof specific to *H. pylori*.

To detect the presence of the 16S rRNA gene in a human blood sample, the extracted DNA is amplified with a polymerase chain reaction (PCR) using a pair of primers specific to the 16S rRNA gene, which includes, but is not limited to, U3 having the DNA sequence of SEQ ID NO:5 and Hp1 having the DNA sequence of SEQ ID NO:6. The PCR is further run by a second pair of primers, which includes, but is not limited to, Hp2 having the DNA sequence of SEQ ID NO:7, and Hp1 having the DNA sequence of SEQ ID NO:6. The PCR product of the 16S rRNA gene that has been detected in the patient's blood sample is about 109 base pairs in length.

The target DNA sequence is further determined by running the amplified DNA in a gel electrophoresis, preferably using an agarose gel, more favorably using a 2.5% agarose gel, and staining the gel with ethidium bromide to determine the size (i.e., base pairs) of the target DNA sequence. The target DNA sequence is further determined by DNA sequencing.

The second embodiment of the present invention includes a method for detecting *Helicobacter pylori* (*H. pylori*)-specific DNA in a blood sample of a human. The method comprises the following steps: (a) obtaining a blood sample from the human; (b) extracting the DNA from the blood sample by a conventional method (such as phenol-chloroform) or a commercially available DNA extraction kit; (c) treating the extracted DNA with a denaturation agent on a solid phase support to form a denatured DNA; (d) providing an *H. pylori* DNA probe, which is labeled with a radioisotope or a fluorescence; and (e) detecting the presence of the *H. pylori* DNA by hybridizing the denatured DNA with the labeled *H. pylori* DNA probe by measuring the radioisotopes or fluorescence on the solid phase support. For radioisotopes, the preferred detection method is by exposing the solid phase support on an X-ray film. For fluorescence, the preferred detection method is by examining the solid phase support under a fluorescence microscope. The preferred blood sample is serum.

The *H. pylori* DNA probe can be prepared by any conventional genetic cloning and expression method. The preferred radioisotope for labeling the *H. pylori* DNA probe includes, but is not limited to, $^{32}P$, $^{3}H$, or $^{14}C$. The preferred fluorescence for labeling the *H. pylori* DNA probe includes, but is not limited to, a digoxigenin- and biotin-labeled DNA probe coupled with fluorescence. The denaturation agent prior to the hybridization. The preferred denaturation agent includes, but is not limited to, alkali solution (e.g., 0.1 to 1 M NaOH), elevated temperatures, organic reagents (e.g., alcohols, amides, amines, ureas, phenols and sulfoxides), or certain inorganic ions (e.g., thiocyanate and perchlorate). The preferred solid phase support is a nitrocellulose filter.

DETAILED DESCRIPTION OF THE INVENTION

Figure 1:
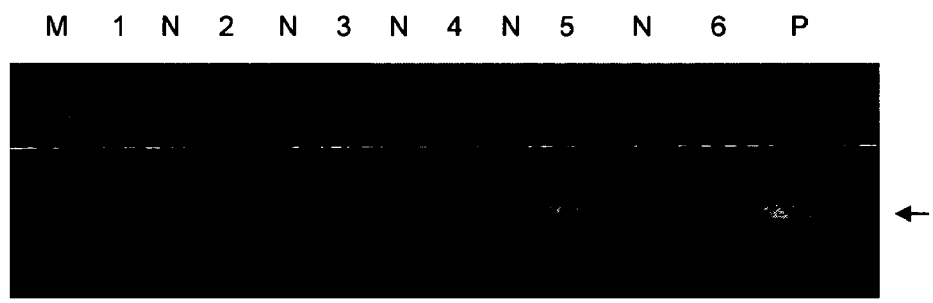
FIG. 1. Photograph of agarose gel showing *H. pylori* Mr26 gene in the blood samples of 4 uninfected humans, marked as 1, 2, 3, and 4, and 2 *H. pylori*-infected patients, marked as 5 and 6. The samples were analyzed in a 2.5% agarose gel electrophoresis and stained with ethedium bromide. M represents DNA Markers (each band represents 100 base pairs); N represents negative control (using water as template); and P represents positive control using *H. pylori* lysate as PCR template. Arrow depicts the PCR product of the Mr26 gene, which is about 190 base pairs.

Although numerous attempts have been reported which provide quantitative and qualitative measurements for *H. pylori* infection in patients, none is directed to the testing of *H. pylori* in blood samples. The major reason is because no investigators has ever assumed that *H. Pylori* antigens could be found in the blood stream until the parent application of the present invention presented evidence that that *H. pylori* antigens can be and have been found in the blood samples of patients with *H. pylori* infection.

Based upon these findings, it is the object of the present invention to utilize the detectable *H. pylori* antigens in blood as tools for diagnosing *H. pylori* infection. In the parent invention, diagnostic methods for detecting *H. pylori* proteins and/or peptide in immunological methods, including, but not limited to, immunoblot, immunoprecipitation, flow cytometry, immuno-electrophoresis, and immunoassays (e.g., enzyme-linked immunosorbent assay [ELISA], radioimmunoassay [RIA], and immunochromatography), are described. In the present invention, a detection of *H. pylori* DNA in the human blood samples is described, which includes the use DNA amplification techniques, such as polymerase chain reaction (PCR), and ligase chain reaction (LCR), as well as DNA hybridization methods, is presented.

In one embodiment of the present invention, a method to detect *H. pylori* DNA in a blood sample with the assistance of DNA amplification techniques is presented. The method includes an extraction of DNA from the blood sample and amplified by a polymerase chain reaction (PCR) or a ligase chain reaction (LCR).

PCR is a technique that amplifies specific DNA sequences with remarkable efficiency. Repeated cycles of denaturation, primer annealing and extension carried out with polymerase, e.g., a heat stable enzyme Taq polymerase, leads to exponential increases in the concentration of desired DNA sequences. Each of the DNA sequences can be separated by agarose gel electrophoresis followed by nucleic acid sequencing. The preferred type of blood sample for PCR is plasma. That is because the heme molecules from the hemoglobin contained within red blood cells may interfere with PCR amplification if hemolysis occurs.

The ligase chain reaction (LCR) is a DNA amplification technique which can be used to detect trace levels of known nucleic acid sequences. LCR involves a cyclic two-step reaction: (1) A high-temperature melting step in which double stranded target DNA unwinds to become single-stranded, and (2) a cooling step in which two sets of adjacent, complementary oligonucleotides anneal to the single-stranded target molecules and ligate together with DNA ligase. The products of the ligation from one cycle serve as templates for the next cycle's ligation reaction. LCR results in the exponential amplification of the ligation products in a manner analogous to the exponential amplification of template in the PCR reaction.

Both PCR and LCR require the findings of *H. pylori* specific primers or oligonucleotides to initiate the nucleic acids chain reaction. Because *H. pylori* strains are highly diverse at a genetic level (Fujimoto et al., *J. Clin. Microbiol.*, (1994), 32:331-334) and individuals can be infected with more than one strain, it is therefore instrumental to design the primers or oligonucleotides based upon the conserved sequence of consensus fragments found in various strains of *H. pylori*. The term "primer" as used herein refers to an oligonucleotide, whether occurring naturally or produced synthetically, which is capable of acting as a point of initiation of nucleic acid synthesis when placed under conditions in which synthesis of a primer product which is complementary to a nucleic acid strand is induced, i.e., in the presence of four different nucleotide triphosphates with appropriate enzymes at a suitable temperature. The term "oligonucleotide" as used herein is defined as a molecule comprised of two or more deoxyribonucleotides and/or ribonucleotides, preferably more than three. Its exact size will depend on many factors, which in turn depend on the ultimate function or use of the oligonucleotide. The oligonucleotide may be derived synthetically or by cloning.

*H. pylori* cells from ATCC strain 43504 have been found to be particularly useful for producing primary antibody against *H. pylori* in stool samples (See U.S. Pat. No. 5,716,791). That is because the antibodies produced through sensitization using cells from strain 43504 can detect the organism across geographic regions and dietary groups. Other *H. pylori* strains, such as ATCC 43571, 43629, 49053, have demonstrated similar antigenic capability. Therefore, it is worthwhile to find consensus fragments among these strains. This can be performed by digesting the extracted nucleic acids from the above mentioned *H. pylori* strains with the same restriction endonuclease(s), followed by running the digested *H. pylori* nucleic acid fragments through an agarose gel electrophoresis. The consensus fragments can be cut out and extracted. The nucleotide sequences of the consensus fragments can be analyzed. The conserved sequence of the consensus fragments can then be used for designing the primers or oligonucleotides for PCR or LCR.

The PCR method provided in the present invention requires the use of a pair of primers specific for detecting a target DNA sequence specific to *H. pylori*. The primers are prepared based upon conserved sequence found in consensus fragments of *H. pylori* strains, such as ATCC strains 43504, 43571, 43629, and 49053. The preferred primers range is from 15 to 25 base pairs (bps), most favorably about 20 bps in length. Better amplification can be obtained when both primers (forward and reverse primers) are the same length and with roughly the same nucleotide composition. The preferred blood sample for PCR is plasma.

In a preferred embodiment, the PCR is conducted by reacting the extracted DNA from human plasma sample (as template) with a pair of primers specific to a target DNA sequence, such as the Mr26 gene, in a reaction solution. The term "target sequence" used herein refers to the "chromosomal DNA or fragments thereof" found in blood samples.

The Mr26 gene (Gene bank accession number: M55507) corresponds to a protein of about 26,000 daltons, which is *H. pylori*-specific. The protein appears to be associated with the soluble fraction of the cells, and antibodies raised against the Mr26 protein are reactive with whole-cell lysates of a variety of *H. pylori* strains. See O'Toole et al., *J. Bacteriology* (1991), 173:505-513, which is incorporated herein by reference. Mr26 protein is present in large quantities in extracts of cells of *H. pylori* and can be purified to homogeneity by ammonium sulfate precipitation followed by gel filtration and reversed-phase chromatography or anion-exchange chromatography. An oligonucleotide derived from the protein sequence of the amino terminus of the Mr26 protein can be expressed in *Escherichia coli* using vector promoters.

The preferred pair of primers for the Mr26 gene includes HPMr3 having the DNA sequence of SEQ ID NO:1 (5'-TGGCGTGTCTATTGACAGCGAGA), and HPMr4 having the DNA sequence of SEQ ID NO:2 (5'-CCTGCTGGGCAT-ACTTCACCAT). The reaction solution further includes a mixture of the nucleic acids (i.e., dATP, dCTP, dTTP, dGTP), Taq DNA polymerase and 1× Taq reaction buffer. The thermal cycle is as follows: an initial incubation temperature at about 94° C. for about 2 minutes; a 30-cycle amplification at (about 94° C. for about 30 seconds; about 56° C. for about 30 seconds; and about 72° C. for about 30 seconds). The final extension is at about 72° C. for about 10 minutes.

The PCR method is preferred to further run by a second round PCR which uses the first PCR product as template and a pair of primers HPMr1 having the DNA sequence of SEQ ID NO:3 (5'-AAGGCGGTATCGGTCAAGT) and HPMr2 having the DNA sequence of SEQ ID NO:4 (5'-CGAAG-CATTTCATCTGCA) in the reaction solution. The thermal cycle program is the same as the first round PCR.

In yet another preferred embodiment, another *H. pylori* DNA gene, 16S rRNA gene, is chosen as the target DNA sequence. A first pair of primers, which includes U3 having the DNA sequence of SEQ ID NO:5 (5'-CAGCAGCCGCG-GTAAT), and Hp1 having the DNA sequence of SEQ ID NO:6 (5'-TGGAGAGACTAAGCC TCC), and a second pair of primers, which includes Hp2 having the DNA sequence of SEQ ID NO:7 (5'-ATTACTGACGCTGATTGC), and Hp1 having the DNA sequence of SEQ ID NO:6 (5'-TGGAGAGACTAAGCC TCC), are chosen. The thermal cycle program for the 16S rRNA gene is the same as that of the Mr26 gene.

The LCR method of the present invention requires the use of a DNA ligase and two sets of oligonucleotide probes which are specific to *H. pylori*. The preferred DNA ligase is Pfu DNA ligase, which is a thermostable DNA ligase isolated from *Pyrococcus furiosus* and is commercially available. The two sets of oligonucleotides for LCR are preferably longer in length than the primers for PCR. Like the PCR primers, the LCR oligonucleotides are derived from conserved sequence of the consensus fragments of *H. pylori* strains, such as ATCC strains 43504, 43571, 43629, and 49053.

LCR is performed by repeated cycles of heat denaturation of a DNA template containing a target sequence, annealing a first set of two adjacent oligonucleotide probes to the target DNA sequence in a unique manner, and a second set of complementary oligonucleotide probes that hybridize to the sequence opposite to the target DNA sequence. The term "target DNA sequence" or "target sequence" used herein refers to the "chromosomal DNA or fragments thereof" found in blood samples. Thereafter, the DNA ligase can covalently link each pair of adjacent probes provided there is complete complementary at the junction of the two adjacent probes.

In addition to PCR or LCR, the presence of *H. pylori* antigens in a blood sample may be detected using nucleic acid hybridization probes. The preferred nucleic acid hybridization probe is no more than about 5,000 bases. The probe sequence is preferably at least substantially complementary to the nucleotide sequence of a consensus fragment among *H. pylori* strains. In addition to the consensus fragment found in various *H. pylori* strains, the probe may be obtained from messenger RNA, from cDNA obtained by reverse transcription of messenger RNA with reverse transcriptase or by cleavage of the genome. After isolation and characterization of the desired probe, the DNA fragment of the probe may be cloned and propagated in host cells. The propagated probe can then be labeled with an atom or inorganic radical, most commonly using radionuclides, but also perhaps heavy metals or fluorescence. It may be feasible to employ an antibody which may bind specifically to the probe hybridized to the single stranded DNA of the *H. pylori* antigen. In this instance, the antibody would be labeled to allow for detection. The same types of labels which are used for the probe may also be bound to the antibody in accordance with known techniques.

The DNA hybridization method (preferably spotted DNA hybridization) described in the present invention requires the preparation of an *H. pylori* DNA probe. The *H. pylori* DNA probe is prepared by cutting out and extracting the DNA fragment corresponding to the target DNA sequence from the *H. pylori* nucleic acid extracts after an agarose gel electrophoresis. The probe normally has at least about 25 bases, more usually at least about 30 bases, and may have up to about 10,000 bases or more, usually having not more than about 5,000 bases. This DNA fragment is then digested with restriction endonucleases and ligated with a vector to form a recombinant plasmid construct, which can transfect eucaryotic or procaryotic host cells. The DNA fragment can be propagated in the host cells and re-isolated, using conventional genetic cloning and isolation methods, which are well-known to one of ordinary skill in the art. The propagated DNA fragment can then be labeled with radioisotope (such as $^{32}P$, $^{3}H$, $^{14}C$, or the like) or fluorescence (such as the use of digoxigenin- and biotin-labeled DNA probes coupled with fluorescence detection methods) and used as a DNA probe, using conventional methods.

The hybridization method is carried out by treating the extracted DNA sample from the human blood sample, preferably serum, with a denaturation agent to denature DNA on a solid phase support such as a nitrocellulose filter. The preferred denaturation agent include, but not limited to, alkali solution, elevated temperatures, organic reagents (e.g., alcohols, amides, amines, ureas, phenols and sulfoxides), or certain inorganic ions (e.g., thiocyanate and perchlorate).

A radioactive label such as $^{32}P$, $^{3}H$, $^{14}C$, or the like may be employed in labeling the probe, although other radioactive labels can also be used as long as they provide for an adequate signal having sufficient half-life. Other labels include ligands, which can serve as a specific binding member to a labeled antibody fluorescers, chemiluminescers, enzymes, antibodies which can serve as a specific binding pair member for a labeled ligand, and the like. A wide variety of labels used in immunoassays can also be used. The choice of the label is governed by the effect of the label on the rate of hybridization and binding of the probe to the sample DNA. It is necessary that the label provide sufficient sensitivity to detect the amount of DNA available for hybridization. Other considerations include the ease of synthesis of the probe, readily available instrumentation, ability to automate, convenience, and the like.

The manner in which the label is bound to the probe varies depending upon the nature of the label. For a radioactive label, a wide variety of techniques can be employed. Commonly employed is nick translation with an $\alpha$-$^{32}P$-dNTP or terminal phosphate hydrolysis with alkaline phosphatase followed by labeling with radioactive $^{32}P$ employing $\gamma$-$^{32}P$-NTP and T4 polynucleotide kinase. Alternatively, nucleotides can be synthesized where one or more of the elements present are replaced with a radioactive isotope, e.g., hydrogen with tritium.

Enzymes of interest as labels include hydrolases, particularly esterases and glycosidases, or oxidoreductase, particularly peroxidase. Fluorescent compounds include fluorescein and its derivatives, rhodamine and its derivatives, dansyl, umbelliferone, etc. Chemiluminescers include luciferin, and 2,3-dihydrophthalazinediones, e.g., luminol.

The hybridization is usually performed by employing the probe to DNA sample affixed to a water insoluble porous support. The DNA sample is denatured so that single stranded nucleic acid is affixed. For lysing, chemical lysing is conveniently employed, usually dilute aqueous alkali, e.g., 0.1 to 1 M NaOH. The alkali can also serve to denature the DNA. Other denaturation agents include, but not limited to, elevated temperatures, organic reagents, e.g., alcohols, amides, amines, urease, phenols and sulfoxides or certain inorganic ions, e.g., thiocyanate and perchlorate.

The labeled DNA probe will then be added to the denatured DNA spotted filter. The filter may then be assayed for the presence of DNA hybrids in the nature of the label. If the label is radioactive, the filter can be exposed to X-ray film. If the label is fluorescence, the filter can be viewed directly using a fluorescence microscope.

The following non-limiting examples are included to illustrate the detection of *H. pylori* antigens in blood.

EXAMPLE 1

Detection of *H. pylori* Mr26 Gene in Blood by PCR

Methods

Circulating DNA from 1 ml of plasma sample was extracted with a commercial kit, the QIAamp blood Mini Kit (QIAGEN). Proteinase K solution and 1 ml of Buffer AL was added to the sample. After incubation at 56° C. for about 1 hour, the sample was passed through a spin column. The majority of the high molecular weight DNA binds to the silica membrane on the spin column. The unbound impurity was washed out and DNA was eluted with 50 µl of 1 mM Tris buffer (pH 8.5). Distilled water was also subjected to DNA extraction and the elute was used as PCR negative control.

*H. pylori* DNA was amplified by two rounds of nested polymerase chain reaction (PCR) to detect the presence of Mr26 gene (Gene bank accession number: M55507). A pair of primers HPMr3 of SEQ ID NO:1 and HPMr4 of SEQ ID NO:2 was used in the first round of PCR and a pair of primers; and a pair of primers HPMr1 of SEQ ID NO:3 and HPMr2 of SEQ ID NO:4 was used in the second round PCR. Briefly, in the first round PCR, 10 µl of the extracted DNA from human blood sample (as template) was reacted with a reaction mixture (50 µl) containing 200 µM dATP, dCTP, dTTP, and dGTP (each), 0.2 µM HPMr3 (SEQ ID NO:1, 5'-TGGCGTGTCTATTGACAGCGAGA), 0.2 µM HPMr4 (SEQ ID NO:2, 5'-CCTGCTGGGCATACTTCACCAT), 2.5 U of Taq DNA polymerase, and 1× Taq reaction buffer. Thermal cycle program was as follows: An initial incubation at 94° C. for 2 min, then a 30-cycle amplification (94° C. for 30 sec, 56° C. for 30 sec, and 72° C. for 30 sec), and then a final extension at 72° C. for 10 min. The second round PCR used a 5-µl aliquot of first PCR product as template and a pair of primers HPMr1 (SEQ ID NO:3, 5'-AAGGCGG-TATCGGTCAAGT) and HPMr2 (SEQ ID NO:4, 5'-CGAAGCATTTCATCTGCA). The thermal cycle program was the same as the first round PCR.

After amplification, PCR products were separated on a 2.5% agarose gel and stained with ethidium bromide. Double-stranded chain-termination DNA sequencing can further be performed after alkali denaturation by using [$^{35}$S]dATP {Amersham Corp., United Kingdom) and Sequenase or Taq polymerase (U.S. Biochemical Corp., Cleveland, Ohio) according to manufacturer's instructions.

Results:

As shown in FIG. 1, plasma samples from 4 uninfected men (labeled as 1, 2, 3 and 4 in the agarose gel) and 2 *H. pylori*-infected patients (labeled as 5 and 6 in the agarose gel) were subjected to DNA extraction and PCR amplification to determine whether the human blood samples contained a fragment of the *H. pylori* Mr26 gene. Patients 5 and 6 showed the same PCR product of Mr26 gene as that of the positive control (P), which contains DNA extract from *H. pylori*. No PCR products were detected in the uninfected men (1, 2, 3) or the negative control (N). The PCR product of Mr26 gene was about 190 bps in length, as shown in FIG. 1.

The DNA sequence analysis of the *H. pylori*-infected patients can be further performed and compared to known DNA sequence for the Mr26 gene according to the data described by O'Toole et al., *J. Bacteriology* (1991), 173: 505-513.

EXAMPLE 2

Detection of the *H. pylori* 16S rRNA Gene in Blood by PCR

Methods:

Circulating DNA from plasma sample of human was isolated as described in Example 1, supra. The target DNA, *H. pylori* 16S rRNA gene, was amplified using the same thermal cycle program as that of Example 1. A first pair of primers, U3 (SEQ ID NO:5, 5'-CAGCAGCCGCGGTAAT) and Hp1 (SEQ ID NO:6, 5'-TGGAGAGACTAAGCCTCC), was used in the first round of PCR (30 cycles); and a second pair of primers, Hp2 (SEQ ID NO:7, 5'-ATTACTGACGCT-GATTGC) and Hp1 (SEQ ID NO:6, 5'-TGGAGAGAC-TAAGCCTCC) was used in the second round of PCR (30 cycles).

Figure 2:
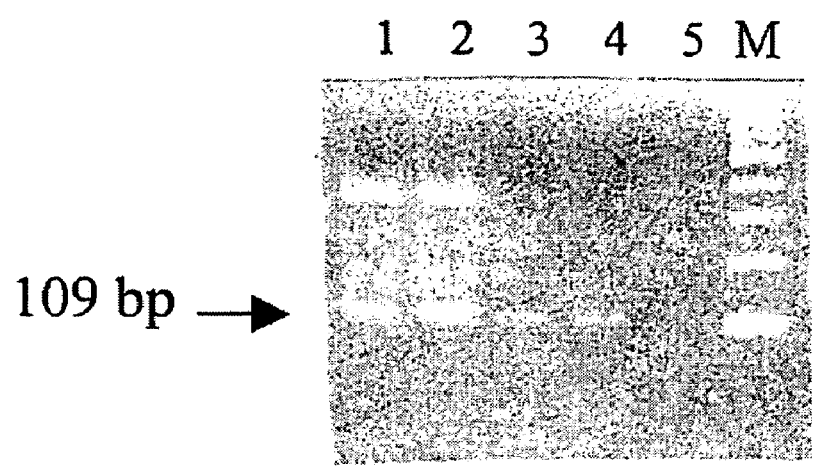
FIG. 2. Photograph of agarose gel showing *H. pylori* 16S rRNA gene in the blood sample of an *H. pylori*-infected patient (lanes 1 and 2, duplicates). Lanes 3 and 4 are positive control (duplicates) using *H. pylori* lysate. Lane 5 is negative control (water). M represents DNA markers (each band represents 100 base pairs). Arrow depicts the PCR product of the 16S rRNA gene, which is about 109 base pairs.

Results:

As shown in FIG. 2, the plasma sample from an *H. pylori*-infected human (Lane 1 and 2, duplicates) showed a DNA band after PCR which was corresponding to that of the positive control sample (Lane 3 and 4, duplicates), which used *H. pylori* as a template, as compared to that of the negative control (Lane 5, water), which showed no such band. The PCR product of the 16S RNA gene was about 109 bps.

EXAMPLE 3

Detection of *H. pylori* DNA in Blood Using LCR Amplification

A ligase chain reaction (LCR) assay requires two sets of two oligonucleotides and a DNA ligase. The first set of oligonucleotides (i.e., Oligo A and Oligo B) are continuous to each other and complementary to one strand of the target DNA duplex. The second set of oligonucleotides (i.e., Oligo C and Oligo D) are complementary to the first set, and therefore occupy adjacent sites on the second strand of the target DNA. All four oligonucleotide probes can be designed according to the conserved sequence of the H. pylori strains and synthesized on an Applied Biosystems (Foster City, Calif.) oligonucleotide synthesizer and purified by PAGE. Oligo A and Oligo D can be radiolabeled at their 5' ends by incubating for 30 minutes at 37° C. in the presence of adenosine 5' ($\gamma$-$^{32}$P) triphosphate and polynucleotide kinase in 50 mM Tris-HCl (pH 7.5), 7 mM $MgCl_2$, and 1 mM dithiothreitol. The polynucleotide kinase can then be inactivated by heating at 70° C. Equal amounts of each of the radiolabeled oligonucleotides probes A and D, and each of the oligonucleotides probes B and C can be added to an eppendorf tube, along with the DNA template extracted from the serum sample. Each tube contains a reaction buffer, consisting of 50 mM bis-Tris pH 6.5, 10 mM $MgCl_2$, 10 mM NH4Cl, 10 mM KCl, 1 mM dithiothreitol and 1 mM NAD. Then, an adequate amount of mineral oil can be overpaid into each tube, and the tubes can be heated to 100° C. for 3 minutes, followed by cooled to 85° C. for 1 minute, and kept at 55° C., while DNA ligase is added. The preferred DNA ligase is Pfu DNA ligase which is derived from *Pyrococcus furiosus*. The reaction tubes can then be placed in a DNA thermocycler (RoboCycler, Stratagene) and cycled between 85° C. and 50° C. 20, 30, or 40 times, for 1 minute at each temperature. An aliquot of each reaction can then be diluted 1:1 with 95% formamide stop dye. This diluted sample can be analyzed on an acrylamide gel.

EXAMPLE 4

Preparation of H. pylori DNA Probes

The H. pylori DNA fragment (normally has at least 25 bases, more usually at least about 30 bases, and may have up to about 10,000 bases or more, but usually has no more than about 5,000 bases) from H. pylori strains can be cut off and extracted from agarose gel after electrophoresis. This DNA fragment can be digested with a restriction endonuclease and ligated with a vector to form a recombinant plasmid construct. For example, the DNA fragment can be digested with ClaI and ligated into a ClaI-digested Pev-Vrf expression vector (Crowl et al., *Gene* (1985), 38:31-38). The recombinant plasmid can then transform a host cell which can be a prokaryotic cell such as *E. coli* RRI, or a eukaryotic cell such as NIH 3T3 cells or HeLa cells. The recombinant plasmids can be propagated through replications in the host cells. The propagated recombinant plasmids can be isolated according to So et al., *Infect. Immun.* (1978), 21:405-41 1. The DNA fragment from H. pylori can be released from the plasmids by digestion with the same restriction endonuclease. The released H. pylori DNA fragment can be confirmed by agarose gel or polyacrylamide electrophoresis. This propagated DNA fragment can then be labeled with radioisotope (such as $^{32}$P, $^3$H, $^{14}$C, or the like) or fluorescence (such as the use of digoxigenin- and biotin-labeled DNA probes coupled with fluorescence detection methods) and used as a DNA probe.

EXAMPLE 5

Preparation of Spotted Hybridization Using H. pylori DNA Probes

Nitrocellulose filters can be sterilized by boiling in water or autoclaved. A single sterile filter can be placed on the surface of agar and spotted with serum which has been treated to liberate its DNA. For example, the serum sample can be lysed with dilute aqueous alkali (e.g., 0.1 to 1 M NaOH). The alkali can also serve to denature the DNA. Other denaturation agents include, but not limited to, elevated temperatures, organic reagents (e.g., alcohols, amides, amines, ureas, phenols and sulfoxides) or certain inorganic ions (e.g., thiocyanate and perchlorate).

After denaturation of the sample, the filter can be washed in an aqueous buffered solution, generally at a pH of about 6 to 8, usually 7. After the lysing, denaturing and washes, the sample DNA spotted filter can be dried at an elevated temperature, generally from about 50° C. to 70° C., to fix the sample DNA on the filter.

The filter can then be incubated at a mildly elevated temperature for a sufficient time with the hybridization solution without the probe to thoroughly wet the filter. Various hybridization solutions may be employed, comprising from about 20 to 60 volume, preferably 30, percent of an inert polar organic solvent. A common hybridization solution employs about 50% formamide, about 0.5 to 1 M sodium chloride, about 0.05 to 0.1 N sodium citrate, about 0.05 to 0.2% sodium dodecylsulfate (SDS), and minor amounts of EDTA, ficoll (about 300-500 kdal), polyvinylpyrrolidone (about 250-500 kdal) and serum albumin. Also included in the hybridization solution may be from about 0.5 to 5 mg/ml of sonicated denatured DNA (e.g., calf thymus or salmon sperm), and optionally from about 0.5 to 2% wt/vol glycine. Other additives may also be included, such as dextran sulfate of from about 100 to 1,000 kdal and in an amount of from about 8 to 15 wt % of the hybridization solution.

The amount of the labeled DNA probe varies widely, depending upon the nature of the label and whether it can reasonably bind to the filter, and the stringency of the hybridization. In general, substantial excesses over stoichiometric of the probe should be employed to enhance the rate of binding of the probe to the fixed sample DNA.

After rinsing the filter at room temperature with a second solution having analogous concentrations of sodium chloride, sodium citrate and SDS as provided in the hybridization solution, the filter may now be assayed for the presence of duplexes in accordance with the nature of the label. Where the label is radioactive, the filter is dried and exposed to X-ray film. If the label is fluorescence, it can be viewed directly using a fluorescence microscope.

The probe need not have perfect complementary to the sequence to which it hybridizes; there may be 30% or more of mismatched pairs. Conditions that influence the formation of DNA hybrids are well known and described in detail by Crosa et al., *J. Bact.* (1973), 115(3):904-911.

Having described the invention in detail and by reference to the preferred embodiments it will be apparent to those skilled in the art that modifications and variations are possible without departing from the scope of the invention as defined in the following appended claims.

What is claimed is:

1. A method for detecting *Helicobacter pylori* (*H. pylori*) DNA in a blood sample of a human comprising:
   obtaining said blood sample from said human;
   extracting said DNA from said blood sample;
   amplifying said extracted DNA in a polymerase chain reaction (PCR) using a pair of primers specific to *H. pylori* to produce amplified DNA;
   detecting the presence of a target DNA sequence in said amplified DNA;
   wherein said target DNA sequence comprises a nucleic acid sequence which is an Mr26 gene of *H. pylori*, and/or fragments of said Mr26 gene that are specific to *H. pylori* and,
   wherein said pair of primers comprises a first primer having the DNA sequence of SEQ ID NO:1 and a second primer having the DNA sequence of SEQ ID NO:2.

2. The method according to claim 1, wherein said PCR is further run by a second pair of primers; wherein said second pair of primers comprises a third primer having the DNA sequence of SEQ ID NO:3 and a fourth primer having the DNA sequence of SEQ ID NO:4.

3. A method for detecting *Helicobacter pylori* (*H. pylori*) DNA in a blood sample of a human comprising:
   obtaining said blood sample from said human;
   extracting said DNA from said blood sample;
   amplifying said extracted DNA in a polymerase chain reaction (PCR) using a pair of primers specific to *H. pylori* to produce amplified DNA;
   detecting the presence of a target DNA sequence in said amplified DNA;
   wherein said target DNA sequence comprises a nucleic acid sequence which is a 16S rRNA of *H. pylori*, and/or fragments of said 16S rRNA gene that are specific to *H. pylori* and,
   wherein said pair of primers comprises a first primer having the DNA sequence of SEQ ID NO:5 and a second primer having the DNA sequence of SEQ ID NO:6.

4. The method according to claim 3, wherein said PCR is further run by a second pair of primers; wherein said second pair of primers comprises a third primer having the DNA sequence of SEQ ID NO: 7, and a fourth primer having the DNA sequence of SEQ ID NO: 6.

* * * * *

SEQUENCE LISTING

<160> NUMBER OF SEQ ID NOS: 7

<210> SEQ ID NO 1
<211> LENGTH: 23
<212> TYPE: DNA
<213> ORGANISM: artificial sequence
<220> FEATURE:
<223> OTHER INFORMATION: primer HPMr3

<400> SEQUENCE: 1
tggcgtgtct attgacagcg aga                                                  23

<210> SEQ ID NO 2
<211> LENGTH: 22
<212> TYPE: DNA
<213> ORGANISM: artificial sequence
<220> FEATURE:
<223> OTHER INFORMATION: primer HPMr4

<400> SEQUENCE: 2
cctgctgggc atacttcacc at                                                   22

<210> SEQ ID NO 3
<211> LENGTH: 19
<212> TYPE: DNA
<213> ORGANISM: artificial sequence
<220> FEATURE:
<223> OTHER INFORMATION: primer HPMr1

<400> SEQUENCE: 3
aaggcggtat cggtcaagt                                                       19

<210> SEQ ID NO 4
<211> LENGTH: 18
<212> TYPE: DNA
<213> ORGANISM: artificial sequence
<220> FEATURE:
<223> OTHER INFORMATION: primer HPMr2

<400> SEQUENCE: 4
cgaagcattt catctgca                                                        18

<210> SEQ ID NO 5
<211> LENGTH: 16
<212> TYPE: DNA
<213> ORGANISM: artificial sequence
<220> FEATURE:
<223> OTHER INFORMATION: primer U3

<400> SEQUENCE: 5
cagcagccgc ggtaat                                                          16

<210> SEQ ID NO 6
<211> LENGTH: 18
<212> TYPE: DNA
<213> ORGANISM: artificial sequence
<220> FEATURE:
<223> OTHER INFORMATION: primer Hp1

<400> SEQUENCE: 6
tggagagact aagcctcc                                                        18

<210> SEQ ID NO 7
<211> LENGTH: 18

```
<212> TYPE: DNA
<213> ORGANISM: artificial sequence
<220> FEATURE:
<223> OTHER INFORMATION: primer Hp2

<400> SEQUENCE: 7
attactgacg ctgattgc                                                   18
```